United States Patent [19]

Varma et al.

[11] Patent Number: 4,707,494
[45] Date of Patent: Nov. 17, 1987

[54] 7-OXABICYCLO(2.2.1)HEPTANE COMPOUNDS USEFUL IN THE TREATMENT OF INFLAMMATION

[75] Inventors: Ravi K. Varma, Belle Mead, N.J.; Carl P. Ciosek, New Hope, Pa.; Eric M. Gordon, Pennington, N.J.

[73] Assignee: E. R. Squibb & Sons, Inc., Princeton, N.J.

[21] Appl. No.: 900,564

[22] Filed: Aug. 26, 1986

[51] Int. Cl.$^4$ .................. A61K 31/557; C07D 307/00
[52] U.S. Cl. ..................................... 514/469; 549/463
[58] Field of Search ......................... 549/463; 514/469

[56] References Cited

U.S. PATENT DOCUMENTS

| | | | |
|---|---|---|---|
| 4,143,054 | 3/1979 | Sprague | 549/463 |
| 4,228,180 | 10/1980 | Sprague | 549/463 |
| 4,254,044 | 3/1981 | Sprague | 549/463 |
| 4,497,827 | 2/1985 | Nelson | 514/381 |
| 4,582,854 | 4/1986 | Hall et al. | 549/463 |
| 4,588,743 | 5/1986 | Harlanger et al. | 549/463 |

FOREIGN PATENT DOCUMENTS 0083204  7/1983  European Pat. Off. .

Primary Examiner—Henry R. Jiles
Assistant Examiner—Bernard I. Dentz
Attorney, Agent, or Firm—Lawrence S. Levinson; Theodore R. Furman, Jr.

[57] ABSTRACT

7-Oxabicyclo(2.2.1)heptane analogs are disclosed having the general formula

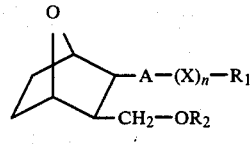

wherein $R_1$ is lower alkyl, alkenyl, substituted alkenyl or alkynyl; $R_2$ is lower alkyl, alkenyl or alkynyl; A is $-CH_2-CH=CH-$ or a single bond; X is $-CH_2$, $-CH(CH_3)$ or $-C(CH_3)_2$; n is an integer from 0 to 9, with the proviso that when A is a single bond, n is an integer from 1 to 9; including all stereoisomers.

These new compounds have been found to be inhibitors of arachidonic acid cyclooxygenase and are therefore useful as antiinflammatory antipyretic and analgesic agents.

10 Claims, No Drawings

7-OXABICYCLO(2.2.1)HEPTANE COMPOUNDS USEFUL IN THE TREATMENT OF INFLAMMATION

FIELD OF THE INVENTION

In a copending application entitled "7-OXABICYCLO(2.2.1)HEPTANE HYDROXAMIC ACID DERIVATIVES USEFUL AS 'DUAL INHIBITORS'" and filed concurrently herewith Ser. No. 900,565, now U.S. Pat. 4,672,075, compounds capable of simultaneously inhibiting the arachidonic acid enzymes 5-lipoxygenase and cyclooxygenase are disclosed.

The present invention relates to 7-oxabicyclo(2.2.1)heptane analogs and more particularly concerns such derivatives which are inhibitors of arachidonic acid cyclooxygenase and as such are useful, for example, as antiinflammatory agents.

SUMMARY OF THE INVENTION

In accordance with the present invention new 7-oxabicyclo(2.2.1)heptane analogs useful as inhibitors of arachidonic acid cyclooxygenase are provided. These new compounds have the general formula

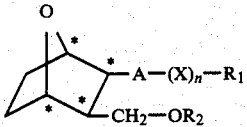     I wherein $R_1$ is lower alkyl, alkenyl, substituted alkenyl or alkynyl; $R_2$ is lower alkyl, alkenyl or alkynyl; A is $-CH_2-CH=CH-$ or a single bond; X is $CH_2$, $CH(CH_3)$ or $C(CH_3)_2$; and n is an integer from 0 to 9, with the proviso that when A is a single bond, n is an integer from 1 to 9; and including all stereoisomers thereof.

DETAILED DESCRIPTION OF THE INVENTION

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an aralkyl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 3 to 8 carbons and a single carbon-carbon double bond, such as 1-propenyl, 2-propenyl, 1-butenyl, 2-butenyl, 3-butenyl and the like.

The lower alkenyl groups can be substituted, for example, with alkyl groups, aryl groups or halogens.

The term "lower alkynyl" or "alkynyl" as used herein by itself or as part of another group includes an unsaturated hydrocarbon group having from 3 to 8 carbon atoms and a single carbon-carbon triple bond, such as 1-propynyl, 2-propynyl, 1-butynyl, 2-butynyl, 3-butynyl and the like.

The term "acyl" as used herein by itself or as part of another group refers to an alkyl carbonyl or alkenyl carbonyl group.

The term "aroyl" as used herein by itself or as part of another group refers to an aryl carbonyl group.

The term "halogen" or "halo" as used herein refers to chlorine, bromine, fluorine or iodine with chlorine being preferred.

Preferred are those compounds of the invention wherein $R_1$ is methyl or [2-methyl-1-propenyl], $R_2$ is hexyl, A is $-CH_2-CH=CH-$, X is $CH_2$ and n=1, 2 or 3.

The various compounds of the invention may be prepared as described below.

To make the compounds of formula I wherein A is $-CH_2-CH=CH-$ and X is $CH_2$, a compound having the formula

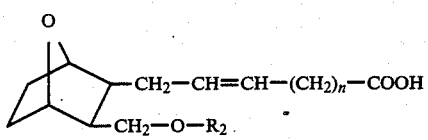     II (prepared as described in U.S. Pat. No. 4,582,854) can be reacted with a suspension of lithium aluminum hydride in a dry organic solvent, e.g. tetrahydrofuran at a temperature within the range of from about 0° to about 25° C. to afford a compound having the formula

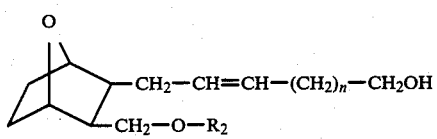     III

Compound III can thereafter be subjected to reaction with a mixture of N-bromosuccinimide and triphenyl phosphine in an organic solvent, e.g. benzene or dichloromethane at about 0° C. to 25° C. to produce the compound

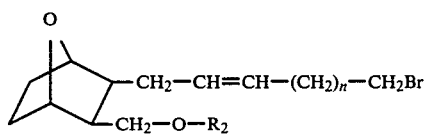   IV

Compound IV, in a dry organic solvent, such as tetrahydrofuran, can next be reacted with lithium aluminum hydride suspended in a solvent, e.g. diethyl ether or tetrahydrofuran, to obtain the compound of the present invention

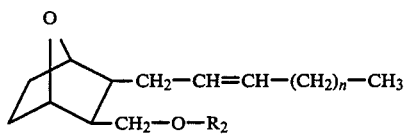   V that is, the compounds of formula I wherein A is —CH$_2$—CH=CH—, X is CH$_2$ and R$_1$ is methyl.

To make compounds of formula I wherein A is —CH$_2$—CH=CH—, X is CH$_2$ and R$_1$ is alkenyl, a compound of the formula

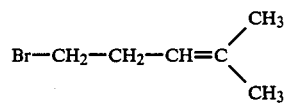   VI is mixed with triphenylphosphine in the presence of an organic solvent, such as acetonitrile or benzene, at a temperature within the range of from about 50° C. to about 90° C. to afford a compound of the formula

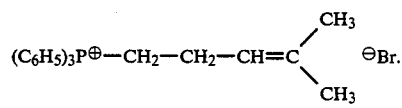   VII

To a suspension of compound VII in a solvent, e.g. tetrahydrofuran, at about 0° C. under an inert atmosphere, e.g. nitrogen, is added a solution potassium-t-amylate in an organic solvent such as toluene. To this is added a solution of the ether aldehyde

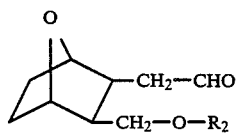   VIII in a dry solvent, e.g. tetrahydrofuran, at room temperature under an inert atmosphere to afford the compound of the invention

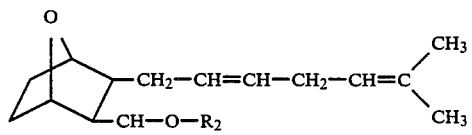   IX that is, the compound of formula I wherein A is —CH$_2$—CH=CH—, X is CH$_2$ and R$_1$ is alkenyl.

An alternative set of reactions for making compounds of the invention wherein R$_1$ is alkyl, alkenyl or substituted alkenyl and R$_2$ is alkyl, alkenyl or alkynyl comprise reacting a compound of the formula

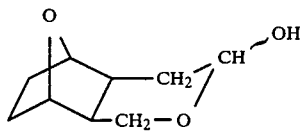   X with a compound of the formula

   XI in the presence of a solvent, e.g. tetrahydrofuran and a base, e.g. potassium t-amylate or n-butyllithium to produce

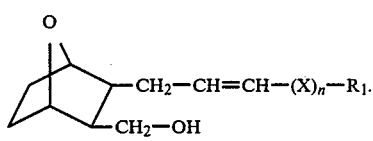   XII

Compound XII can thereafter be reacted with

R$_2$O Mesylate   XIII in the presence of an inorganic base, e.g. potassium hydroxide and an organic solvent, e.g. xylene, to afford compounds of the invention

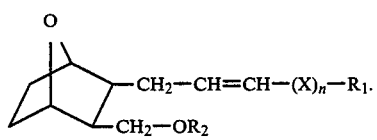   XIV

The compounds of this invention have four centers of asymmetry as indicated by the asterisks in formula I. However, it will be apparent that each of the formulae set out about which do not include asterisks still represent all the possible stereoisomers thereof. All of the various stereoisomeric forms are within the scope of the present invention.

The various stereoisomeric forms of the compounds of the invention, namely, cis-endo, cis-exo and all trans forms and stereoisomeric pairs may be prepared as shown in the working Examples which follow and by employing starting materials and following the procedures as outlined in U.S. Pat. No. 4,582,854. Examples of such stereoisomers are set out below.

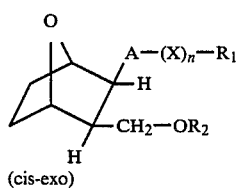   Ia (cis-exo)

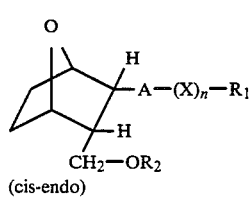   Ib (cis-endo)

-continued

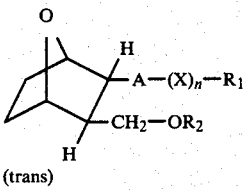
Ic
(trans)

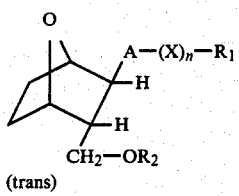
Id
(trans)

The nucleus in each of the compounds of the invention is depicted as

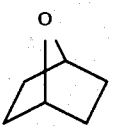

for matter of convenience; it will also be appreciated that the nucleus in the compounds of the invention may be depicted as

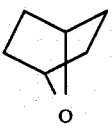

The compounds of the invention are arachidonic acid cyclooxygenase inhibitors. The administration of compounds of this invention to humans or animals provides a method for treating inflammation. Arthritis is preferably treated but any type of inflammatory disease where prostaglandins are involved as pharmacological mediators can be treated. In addition, compounds of the invention are analgesics and antipyretics. For example, the compounds of this invention can be used for treatment of such conditions as rheumatoid arthritis, osteoarthritis, headaches, fevers and sunburns.

An effective but essentially non-toxic quantity of the compound is employed in treatment.

The compounds of the invention can be administered orally, parenterally or topically to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, suspension, cream, lotion or ointment containing about 1 to about 5000 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention.

EXAMPLE 1

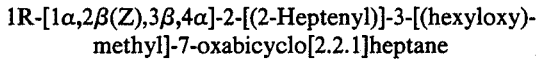

A suspension of lithium aluminum hydride (76 mg, 1.0 mmole) in dry tetrahydrofuran (hereinafter THF) was cooled and stirred under nitrogen atmosphere and a solution of 1R-[1α,2β(Z),3β,4α]-7-2]-[3-[(hexyloxy)-methyl]-7-oxabicyclo(2.2.1)hept-2yl]-hept]-5-enol (200 mg, 0.52 mmole) in 2.0 ml of dry THF was added. After 5 minutes the mixture was refluxed for 2 hours. It was then re-cooled and decomposed by the careful addition of 10 ml of 20% hydrochloric acid. It was further diluted with brine (20 ml) and extracted three times with ether. The extracts were combined, washed with brine and a dilute solution of sodium bicarbonate, dried over anhydrous magnesium sulfate and evaporated to afford an oil. This was chromatographed to afford 128 mg of 1R-[1α,2β(Z),3β,4α]-2-[(2-Heptenyl)-3-[(hexyloxy)-methyl]-7-oxabicyclo[2.2.1]heptane as an oil.

EXAMPLE 2

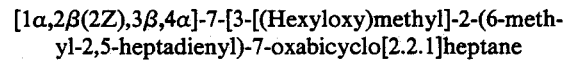

A. (4-Methyl-3-pentenyl)triphenylphosphonium bromide

A mixture of 5-bromo-2-methyl-2-pentene (489.2 mg, 3 mmole) and triphenylphosphine (787 mg, 3 mmole) in 6 ml of acetonitrile was stirred at 95° C. (oil bath temperature) under nitrogen for 20 hours. The solvent was evaporated by a stream of nitrogen. The residue was dried in vacuo at room temperature to give a foam. This was rinsed with ethyl ether to give a white solid which was filtered, washed with ethyl ether and dried in vacuo at 100° C. for 4 hours to afford 905 mg of (4-methyl-3-pentenyl)triphenylphosphonium bromide.

B.

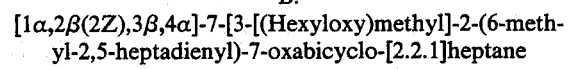

A suspension of (4-methyl-3-pentenyl)triphenylphosphonium bromide (850 mg, 2 mmole) in 15 ml of dry THF was chilled to 0° C. under nitrogen. A solution of 1.68M potassium-t-amylate in toluene (0.81 ml, 1.36 mmole) was added dropwise. The resulting solution was warmed to room temperature and stirred for 30 minutes. To the so-formed solution was added a solution of [1α,2β,3β,4α]-2-[[3-(Hexyloxy)methyl]-7-oxabicyclo-(2.2.1)hept-2yl]-acetaldehyde (203 mg, 0.8 mmole) in 2 ml of dry THF and stirred at room temperature under nitrogen for 2 hours. The resulting solution was acidified with 5% hydrochloric acid to a pH of 2. The solution was evaporated in vacuo to remove the THF. The residue was diluted with 10 ml of water, saturated with sodium chloride and extracted four times with ethyl ether. The combined extracts were dried over anhydrous magnesium sulfate and evaporated. The residue was chromatographed to produce 175 mg of [1α,2β(2Z),3β,4α]-7-[3-[(Hexyloxy)methyl]-2-(6-methyl-2,5-heptadienyl)-7-oxabicyclo-[2.2.1]heptane.

EXAMPLES 3 TO 15

The following additional compounds within the scope of the present invention may be prepared by employing the teachings as outlined above and in the working examples.

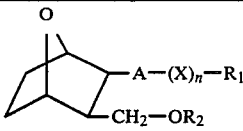

| Ex. No. | $R_1$ | $R_2$ | A | X | n |
|---|---|---|---|---|---|
| 3 | $-C_3H_7$ | $-CH_2-C{\equiv}C-CH_3$ | $-CH_2-CH{=}CH-$ | $CH_2$ | 3 |
| 4 | $-CH{=}\overset{Br}{C}-CH_2-CH_3$ | $-CH_2-C{\equiv}C-CH_3$ | $-CH_2-CH{=}CH-$ | $CH_2$ | 6 |
| 5 | $-C_4H_9$ | $-C_2H_5$ | $-CH_2-CH{=}CH-$ | $CH_2$ | 2 |
| 6 | $-C_5H_{11}$ | $-CH{=}CH-CH_3$ | $-CH_2-CH{=}CH-$ | $CH_2$ | 1 |
| 7 | $-C_2H_5$ | $-C_3H_7$ | — | — | 0 |
| 8 | $-C_2H_5$ | $-C_3H_7$ | — | $CH(CH_3)$ | 2 |
| 9 | $-CH{=}C{<}^{CH_3}_{CH_3}$ | $-C_2H_5$ | $-CH_2-CH{=}CH-$ | $CH_2$ | 4 |
| 10 | $-CH_2-C{\equiv}C-CH_3$ | $CH_2-CH{=}CH-C_2H_5$ | $-CH_2-CH{=}CH-$ | $C(CH_3)_2$ | 1 |
| 11 | $-CH_3$ | $-C_2H_5$ | $-CH_2-CH{=}CH-$ | $CH_2$ | 5 |
| 12 | $-CH{=}CH-\overset{Cl}{CH}-CH_3$ | $-C_7H_{15}$ | $-CH_2-CH{=}CH-$ | $CH_2$ | 2 |
| 13 | $-CH_2-CH{=}CH-CH_2$-phenyl | $-C_3H_7$ | — | $C(CH_3)_2$ | 2 |
| 14 | $-C_3H_7$ | $-C_3H_7$ | $-CH_2-CH{=}CH-$ | $CH_2$ | 3 |
| 15 | $-CH{=}CH-CH_3$ | $CH_2-CH{=}CH-CH_3$ | $-CH_2-CH{=}CH-$ | $CH_2$ | 4 |

What is claimed:

1. A compound of the formula

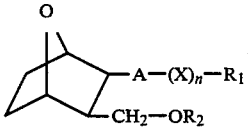

wherein $R_1$ is lower alkyl, alkenyl, or alkynyl of 3-8 carbon atoms; $R_2$ is lower alkyl, alkenyl or alkynyl of 3-8 carbon atoms; A is $-CH_2-CH{=}CH-$ or a single bond; X is $-CH_2-$, $-CH(CH_3)$ or $-C(CH_3)_2$; n is an integer from 0 to 9; with the proviso that when the A is a single bond, n is an integer from 1 to 9 including all stereoisomers thereof;

wherein the term lower alkyl or alkyl refers to both straight and branched chain radicals of up to 12 carbons, as well as such groups including a halo-substituent, an alkoxy substituent, halophenyl substituent, a halonaphthyl substituent, a cycloalkyl substituent, an alkylcycloalkyl substituent, an alkylamino substituent, an alkanoylamino substituent, a phenylcarbonylamino substituent, a naphthylcarbonylamino substituent, a nitro substituent, a cyano substituent, a thiol substituent or an alkylthio substituent;

and the term alkenyl contains 3 to 8 carbon atoms and can be substituted with alkyl, or halogen.

2. A compound of claim 1 wherein $R_1$ is lower alkyl, $R_2$ is lower alkyl, A is $-CH_2-CH{=}CH-$, X is $-CH_2$ and n=3.

3. A compound of claim 1 wherein $R_1$ is alkenyl, $R_2$ is lower alkyl, A is $-CH_2-CH{=}CH-$, X is $-CH_2$ and n=1.

4. A compound of claim 1 having the name 1R-[1α,2β(5Z),3β,4α]]-2-(2-Heptenyl)-3-[(hexyloxy)methyl]-7-oxabicyclo[2.2.1]heptane.

5. A compound of claim 1 having the name 1α,2β(2Z),3β,4α]-7-[3-[(hexyloxy)methyl]-2-(6-methyl-2,5-heptadienyl)-7-oxabicyclo-[2.2.1]heptane.

6. A composition for treating inflammation in a mammalian species comprising administration of an effective amount of a compound as defined in claim 1 and a pharmaceutically acceptable carrier therefor.

7. A method of inhibiting arachidonic acid cyclooxygenase in mammalian species which comprises administering to the circulatory system of host an effective amount of a compound as defined in claim 1.

8. The method of claim 7 wherein said compound is administered in an amount within the range of from about 1 to about 100 mg/kg.

9. A method for treating fever, pain, and inflammation in a mammalian species in need of such treatment, which comprises administering to host an effective amount of a compound as defined in claim 1.

10. A method of treating sunburn in a mammalian species in need of such treatment which comprises administering to host topically an effective amount of a compound as defined in claim 1 in a pharmaceutically acceptable carrier.

* * * * *